US008041156B2

(12) United States Patent
Dennison et al.

(10) Patent No.: US 8,041,156 B2
(45) Date of Patent: Oct. 18, 2011

(54) SINGLE-FRAME AND MULTI-FRAME IMAGE DATA CONVERSION SYSTEM AND METHOD

(75) Inventors: Donald K. Dennison, Waterloo (CA); John J. Potwarka, Waterloo (CA)

(73) Assignee: AGFA Inc, Toronto (CA)

( * ) Notice: Subject to any disclaimer, the term of this patent is extended or adjusted under 35 U.S.C. 154(b) by 1141 days.

(21) Appl. No.: 11/443,359

(22) Filed: May 31, 2006

(65) Prior Publication Data

US 2007/0280560 A1    Dec. 6, 2007

(51) Int. Cl.
*G06K 9/60* (2006.01)
*G06F 15/16* (2006.01)
*G06F 3/00* (2006.01)

(52) U.S. Cl. ............ 382/306; 709/230; 725/52
(58) Field of Classification Search ........... 382/306
See application file for complete search history.

(56) References Cited

U.S. PATENT DOCUMENTS

| | | | |
|---|---|---|---|
| 6,836,293 B2 | 12/2004 | Itoh et al. | |
| 2002/0015104 A1 | 2/2002 | Itoh et al. | |
| 2002/0091584 A1* | 7/2002 | Clark et al. | 705/26 |
| 2002/0104093 A1* | 8/2002 | Buehl et al. | 725/98 |
| 2002/0107973 A1* | 8/2002 | Lennon et al. | 709/231 |
| 2002/0152267 A1* | 10/2002 | Lennon | 709/203 |
| 2002/0188621 A1* | 12/2002 | Flank et al. | 707/104.1 |
| 2003/0093434 A1* | 5/2003 | Stickler | 707/103 R |
| 2003/0229520 A1 | 12/2003 | Wise et al. | |
| 2004/0003403 A1* | 1/2004 | Marsh | 725/53 |
| 2004/0139222 A1* | 7/2004 | Slik et al. | 709/236 |
| 2004/0158584 A1* | 8/2004 | Necsoiu et al. | 707/104.1 |
| 2004/0177319 A1* | 9/2004 | Horn | 715/501.1 |
| 2004/0244039 A1* | 12/2004 | Sugahara et al. | 725/52 |
| 2006/0287890 A1* | 12/2006 | Stead et al. | 705/3 |

FOREIGN PATENT DOCUMENTS

WO   WO 2005 062715   7/2005

OTHER PUBLICATIONS

PCT Written Opinion/International Search Report dated Oct. 25, 2007.
Computed Tomography, Wikipedia The Free Encyclopedia, http://en.wikipedia.org/wiki/CT_scan, pp. 1 to 9, May 12, 2006.
The DICOM Standard, DICOM Introduction and Free Software, http://www.sph.sc.edu/comd/rorden/dicom.html, pp. 1 to 6, May 12, 2006.

* cited by examiner

*Primary Examiner* — David Zarka
(74) *Attorney, Agent, or Firm* — Bereskin & Parr LLP; Isis E. Caulder

(57) ABSTRACT

A system and method for converting between a plurality of single-frame image data objects and a multi-frame image data object. Meta-data attributes common to each single-frame image data object from a source are considered to be shared meta-data attributes and associated with a multi-frame image data object. Perframe meta-data attributes and pixel data are not shared and are individually stored within the multi-frame image data object. In reverse, the number of perframe meta-data attributes within a multi-frame image data object from a source are examined and the corresponding number of single-frame image data objects are created. The shared meta-data attributes are copied into each single-frame image data object along with associated perframe meta-data attributes and pixel data. This conversion process can be applied as images are transmitted to the image manager/archive from the modality, as studies are retrieved from the image manager/archive, and as studies are requested.

26 Claims, 11 Drawing Sheets

SINGLE-FRAME AND MULTI-FRAME IMAGE DATA CONVERSION SYSTEM AND METHOD

FIELD

The embodiments described herein relate generally to the field of data conversion and more particularly to the conversion of image data objects.

BACKGROUND

Medical imaging has been an expanding field for several decades. With increasing diagnostic tools, increasing population, more wide-spread access to medical treatment, and the desirability of sharing information between doctors and professionals, medical imaging is likely to continue growing. To address this continued growth, and the subsequent inconveniences of paper and other fixed forms of medical image storage, the medical community has increasingly turned to digital forms of image storage.

Picture Archiving and Communications Systems (PACS) are a common example of a digital image system. These systems connect elements such as imaging modalities, storage databases or areas, clients that use the medical image data, and data processing devices to create a network of imaging technology. Such systems then provide easier remote diagnosis and data access, sharing of information between health-care professionals, and ultimately a better health-care system.

Currently, large volume Computed Tomography (CT), Magnetic Resonance (MR) and X-Ray Angiography (XA) DICOM studies utilized by local PACS networks pose a significant image data management problem due to the large number of image data files that must be transferred within and between local PACS networks. A typical image dataset can easily contain over 2000 slices that translates into a similar number of image data files.

Each image data file can be expressed as two logical parts. One part is the meta-data that represents a set of attributes that describes the image. The other part is known as pixel data that represents the displayed image. Each image data file in an image dataset contains a significant amount of common meta-data such as patient, study, and image attributes. Since each individual image data file contains its own common meta-data, this results in a substantial amount of redundant meta-data being stored in the image display caches and being mapped into the database, as is commonly the case within local PACS networks.

To address these issues, a new Digital Imaging and Communications in Medicine (DICOM) image data standard has been developed which defines a new multi-frame DICOM image data object into which any number of CT, MR or XA slices can be combined. These new multi-frame DICOM image data objects are called Enhanced Multi-Frame image data objects. The term multi-frame simply refers to a DICOM image data object that contains a number of distinct but related images in a single file. This object, similar to the conventional single frame object contains both meta-data and pixel data. However, meta-data, in the case of the new multi-frame DICOM image data object, is combined, grouped by shared attributes. This approach removes the inefficiency of the redundancy and significantly decreases the storage required for image data object meta-data.

However, the adoption rate of the new DICOM image data standard by CT, MR or XA imaging modality vendors has been slow. In addition, the number of existing large volume CT, MR, or XA equipment installed within medical facilities such as hospitals is substantial. Since the cost of CT, MR and XA imaging modalities is high, the rate at which hospitals upgrade these systems is also slow. Given this, support for the new Enhanced Multi-Frame image data objects will also be slow. Finally, and potentially more importantly, large volumes of image data objects that were created using the old DICOM data standard will be stored within PACS systems for many years, even after the old data standard imaging modalities are upgraded to the new Enhanced Multi-Frame standard. Consequently, large volume image data studies stored as individual slices will be commonplace for some time with the associated inefficiencies.

SUMMARY

The embodiments described herein provide in one aspect a system for storing image data objects and for retrieving the image data objects, the system comprising:
  a memory for storing imaging data objects, each image data object being stored in a single-frame image data standard or a multi-frame image data standard; and
  a processor coupled to the memory configured to:
    detect a data transmission negotiation from an external imaging device for a workflow request for one or more requested image data objects;
    when a data transmission negotiation is detected, determine a first set of negotiations particulars of the negotiation, the first set of negotiation particulars comprising an indication of the image data standard supported by the external imaging device and an indication of a type of workflow request;
    determine whether to convert the one or more requested image data objects based on the first set of negotiation particulars; and
    if the requested image data objects is to be converted, determining whether to convert the requested image data objects to the single-frame image data standard or the multi-frame image data standard;
  wherein the external imaging device supports at least one of the single-frame image data standard or the multi-frame image data standard;
  wherein the workflow request type is a retrieve type for retrieving one or more requested image data objects from the memory or a store type for storing one or more requested image data objects to the memory;
  wherein each single-frame image data object comprises pixel data associated with one or more meta-data attributes; and
  wherein the processor converting a first requested single-frame image data object and a second requested single-frame image data to the multi-frame image data standard comprises the steps of:
    (i) determining one or more shared meta-data attributes of the first and second requested image data objects by determining which of the one or more meta-data attributes of the first requested image data object and the one or more meta-data attributes of the second requested image data object are the same;
    (ii) associating the shared meta-data attributes from (i) as one entity within a multi-frame image data object; and
    (iii) associating the pixel data of the first requested image data object and the pixel data of the second requested image data object as separate entities within the multi-frame image data object.

The embodiments described herein provide in another aspect a memory and for retrieving the image data objects from the memory, each image data object being in a single-frame image data standard or a multi-frame image data standard, the method comprising:

detecting a data transmission negotiation from an external imaging device for a workflow request for one or more requested image data objects;

when a data transmission negotiation is detected, determining a first set of negotiations particulars of the negotiation, the first set of negotiation particulars comprising an indication of the image data standard supported by the external imaging device and an indication of a type of workflow request;

determining whether to convert the one or more requested image data objects based on the first set of negotiation particulars; and if the requested image data objects is to be converted, determining whether to convert the requested image data objects to the single-frame image data standard or the multi-frame image data standard;

wherein the external imaging device supports at least one of the single-frame image data standard or the multi-frame image data standard; and wherein the workflow request type is a retrieve type for retrieving one or more requested image data objects from the memory or a store type for storing one or more requested image data objects to the memory;

wherein each single-frame image data object comprises pixel data associated with one or more meta-data attributes; and wherein converting a first requested single-frame image data object and a second requested single-frame image data from the single-frame image data standard to the multi-frame image data standard comprises the steps of:

(i) determining one or more shared meta-data attributes of the first and second requested image data objects by determining which of the one or more meta-data attributes of the first requested image data object and the one or more meta-data attributes of the second requested image data object are the same;

(ii) associating the shared meta-data attributes from (i) as one entity within a multi-frame image data object; and (iii) associating the pixel data of the first requested image data object and the pixel data of the second requested image data object as separate entities within the multi-frame image data object.

The embodiments described herein provide in another aspect a system for storing image data objects and for retrieving the image data objects, the system comprising:

a memory for storing imaging data objects, each image data object being stored in a single-frame image data standard or a multi-frame image data standard; and a processor coupled to the memory configured to:

detect a data transmission negotiation from an external imaging device for a workflow request for one or more requested image data objects;

when a data transmission negotiation is detected, determine a first set of negotiations particulars of the negotiation, the first set of negotiation particulars comprising an indication of the image data standard supported by the external imaging device and an indication of a type of workflow request;

determine whether to convert the one or more requested image data objects based on the first set of negotiation particulars; and if the requested image data objects is to be converted, determining whether to convert the requested image data objects to the single-frame image data standard or the multi-frame image data standard;

wherein the external imaging device supports at least one of the single-frame image data standard or the multi-frame image data standard;

wherein the workflow request type is a retrieve type for retrieving one or more requested image data objects from the memory or a store type for storing one or more requested image data objects to the memory;

wherein each multi-frame image data object comprises a set of one or more shared meta-data attributes and first and second pixel data; and wherein the processor converting a requested multi-frame image data object to the single-frame image data standard comprises the steps of:

(i) associating the shared meta-data attributes and the first pixel data of the requested multi-frame image data object within a first single-frame image data object; and (ii) associating the share meta-data attributes and the second pixel data of the requested multi-frame image data object within a second single-frame image data object.

The embodiments described herein provide in another aspect a method for storing image data objects at a memory and for retrieving the image data objects from the memory, each image data objects being in a single-frame image data standard or a multi-frame image data standard, the method comprising:

detecting a data transmission negotiation from an external imaging device for a workflow request for one or more requested image data objects;

when a data transmission negotiation is detected, determining a first set of negotiations particulars of the negotiation, the first set of negotiation particulars comprising an indication of the image data standard supported by the external imaging device and an indication of a type of workflow request;

determining whether to convert the one or more requested image data objects based on the first set of negotiation particulars; and if the requested image data objects is to be converted, determining whether to convert the requested image data objects to the single-frame image data standard or the multi-frame image data standard;

wherein the external imaging device supports at least one of the single-frame image data standard or the multi-frame image data standard; and wherein the workflow request type is a retrieve type for retrieving one or more requested image data objects from the memory or a store type for storing one or more requested image data objects to the memory.

wherein each multi-frame image data object comprises a set of one or more shared meta-data attributes and first and second pixel data; and wherein converting a requested multi-frame image data object to the single-frame image data standard comprises the steps of:

(i) associating the shared meta-data attributes and the first pixel data of the requested multi-frame image data object within a first single-frame image data object; and (ii) associating the share meta-data attributes and the second pixel data of the requested multi-frame image data object within a second single-frame image data object.

Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

Figure 1:
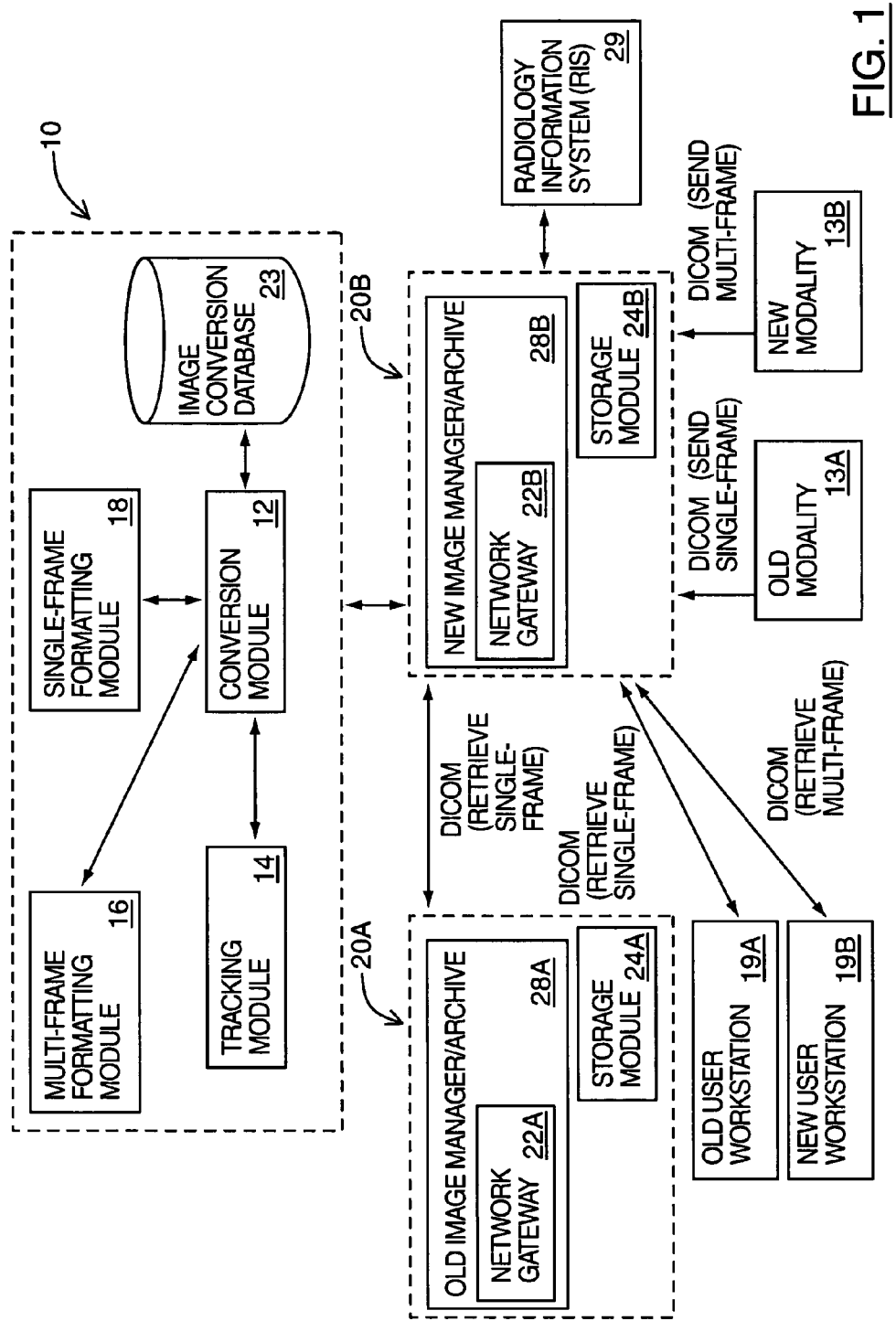
FIG. 1 is a block diagram of the components of an exemplary embodiment of an image data conversion system.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), at least one input device, and at least one output device. For example and without limitation, the programmable computers may be a personal computer, laptop, personal data assistant, and cellular telephone. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Reference is first made to FIG. 1, which illustrates the components of an image data conversion system 10 made in accordance with an exemplary embodiment. Image data conversion system 10 includes a conversion module 12, a tracking module 14, a multi-frame formatting module 16, a single-frame formatting module 18, and an image conversion database 23. For illustrative purposes, studies will be assumed to be generated by both an old standard imaging modality 13A according to a single-frame data object standard and by a new standard imaging modality 13B according to a multi-frame data object standard. Also, an old standard image manager/archive 28A operates according to the single-frame data object standard and a new standard image manager/archive 28B operates according to the multi-frame data object standard. In the exemplary embodiment, the image data conversion system 10 is associated with the new image manager/archive 28B and performs automatic and real time image data conversion as needed between the single-frame data object format utilized by older imaging equipment, such as the old standard modality 13A, the old standard image manager/archive 28A, an old standard user workstation 19A and the multi-frame data object format utilized by newer imaging equipment such as the new standard image manager/archive 28B and a new standard user workstation 19B.

The old standard imaging modality 13A generates conventional medical image data (e.g. X-ray images, CT scan images, MRI images, etc.) into in digital format (i.e. an image data file) according to the old single-frame DICOM standard. Accordingly, the old imaging modality 13A sends single-frame image data to the new image manager/archive 28B using the old single-frame DICOM protocol.

The new standard imaging modality 13B generates conventional medical image data (e.g. X-ray images, CT scan images, MRI images, etc.) into in digital format (i.e. an image data file) according to the enhanced DICOM standard. Accordingly, the new imaging module 13B sends multi-frame image data to the new image manager/archive 28B using the Enhanced Multi-Frame DICOM protocol.

Figure 2:
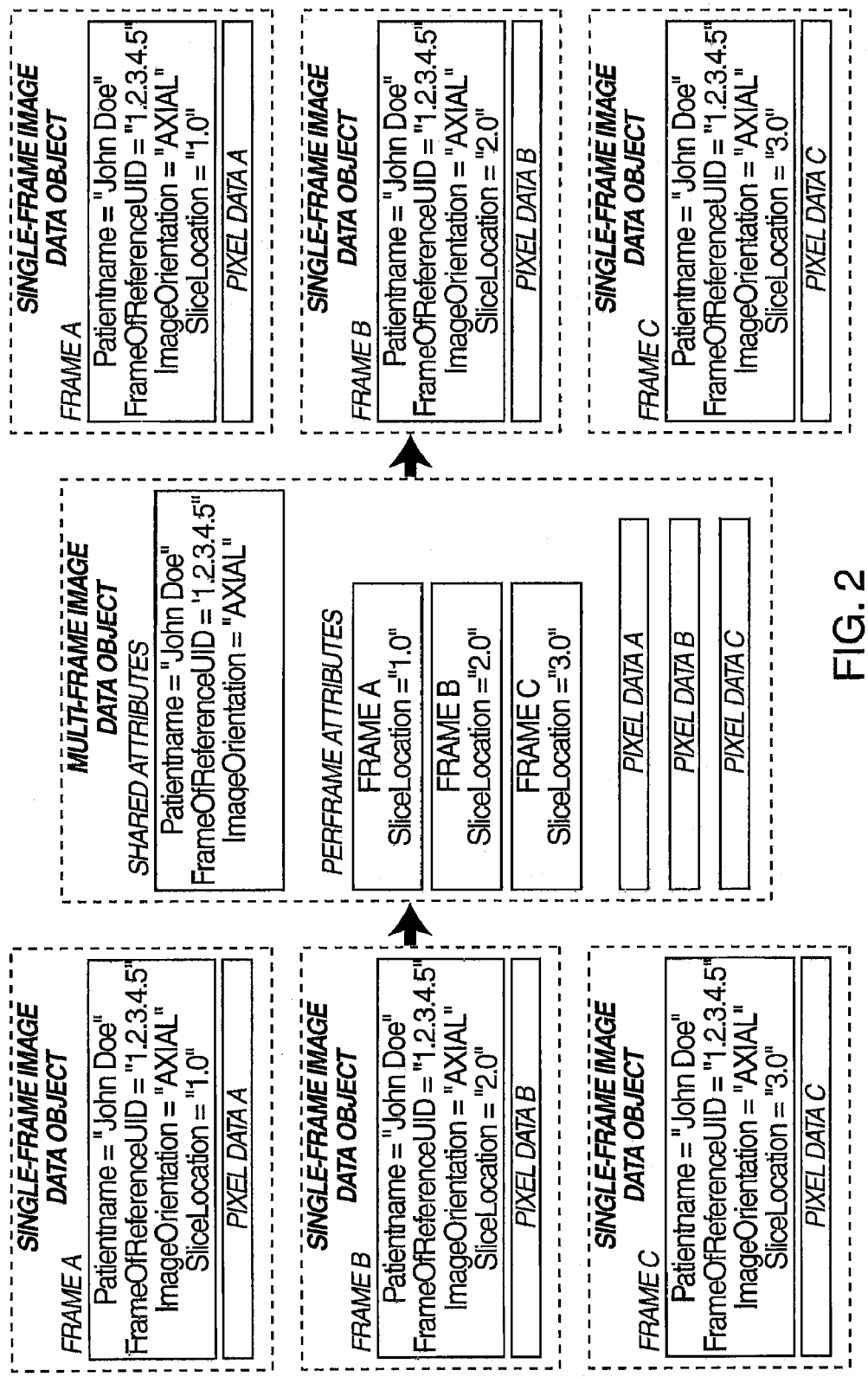
FIG. 2 is a schematic diagram illustrating one exemplary embodiment of the multi-frame image data formatting and the single frame formatting conducted by the image data conversion system of FIG. 1.

Referring now to FIGS. 1 and 2, as previously mentioned, the new DICOM image data standard which uses new Enhanced Multi-Frame image data objects into which any number of CT, MR or XA slices can be combined will be described. Specifically, FIG. 2 is a schematic diagram that illustrates an example of the multi-frame image data formatting and the single frame formatting conducted by the image data conversion system 10. The term "multi-frame" should be understood to refer to a DICOM image data object that contains a number of distinct but related images in a single image file. This object, similar to the conventional single frame object contains both meta-data and pixel data. However, meta-data, in the case of the new multi-frame DICOM image data object, is combined and grouped by shared meta-data attributes. In this way, the overall storage size of the multi-frame image object will be significantly smaller than the equivalent single-frame image dataset since the redundancy previously created by repeated instances of shared meta-data attributes within the single-frame image objects has been eliminated.

Further, in the present disclosure, it should generally be understood that the term "single-frame image dataset" represents a set of single-frame image data objects, each single-frame image data object containing image meta-data and pixel data. Also, it should be understood that the term "multi-frame image object" contains image meta-data and pixel data. Finally, it should be understood that all of these terms related to various kinds of digital image entities (e.g. series, studies, images, etc.) without exclusion.

The local PACS networks 20A and 20B are old and new conventional PACS networks, respectively. Old PACS network 20A includes an old image manager/archive 28A and an old storage module 24A. New PACS network 20B includes a new image manager/archive 28B and a new storage module 24B. Each network gateway 22A and 22B includes an image manager 28A and 28B which manages communication between and amongst external imaging equipment. The storage modules 24A and 24B are used to archive storage data and can implement such archiving imaging methods such as for example, hierarchical storage management (HSM) or store and remember archiving. Typically, the network gateway 22A or 22B receives a request for image data from a client, determines the location of the requested image data within the local PACS network 20A or 20B (possibly by checking with other external PACS networks) and provides the client access to the requested image data.

Since it is more efficient for the new-style multi-frame image data object to be managed by local PACS network(s) 20, the image data conversion system 10 has been designed to be configurable so that multi-frame formatting can be automatically conducted upon receipt of, or import by, the new image manager/archive 28B of single-frame image data objects from old standard imaging equipment since multi-frame formatting is substantially more time consuming than single-frame formatting.

Further, the image data conversion system 10 has also been designed to be configurable so that single-frame formatting is automatically conducted upon transmission of, or export by, the new image manager/archive 28B of single-frame image data objects to old standard imaging equipment. The image data conversion system 10 can also be configured to allow manual conversion of image data files between single-frame and multi-frame image data objects preferably triggered by a user action as will be described.

The conversion module 12 coordinates the operation of the tracking module 14, the multi-frame formatting module 16, the single-frame formatting module 18 and the image conversion database 23 to provide interfacing between imaging equipment that is not configured to utilize the new Enhanced Multi-Frame standard such as, for example, the old standard modality 13A, the old standard image manager/archive 28A, and the old standard user workstation 19A and imaging equipment that is configured to utilize the new Enhanced Multi-Frame standard, such as the new standard image manager/archive 28B and the new standard user workstation 19B.

The tracking module 14 determines whether a DICOM negotiation has occurred between the new standard PACS 20B and another imaging equipment device, and if so then determines particulars associated with the DICOM negotiation. The conversion module 12 then uses this information along with relevant system configuration data and conversion rules stored in image conversion database 23 to determine whether image data conversion is necessary and if so whether the conversion should involve multi-frame formatting or single-frame formatting or none at all. In this way, the tracking module 14 monitors instances of DICOM negotiations between various imaging equipment and determines the particulars associated with the DICOM negotiation and provides this information to the conversion module 12.

The multi-frame formatting module 16 is used to convert a plurality of single-frame image data objects within an image dataset into a multi-frame image data object. The multi-frame formatting module 16 reviews the meta-data associated with each individual single-frame image data object and determines which meta-data elements are shared meta-data attributes and which are perframe meta-data attributes as will be further described. Shared meta-data attributes are then mapped together as one set of shared attributes within the multi-frame image data object. The multi-frame formatting module 16 then maps the perframe meta-data attributes and the individual single-frame object pixel data separately into the multi-frame image data object.

The single-frame formatting module 18 is used to convert a multi-frame image data object into a single-frame image data object. The single-frame formatting module 18 maps the individual per-frame meta-data attributes and the individual pixel data into an equivalent number of single-frame data objects. The single-frame formatting module 18 then maps individual copies of the shared meta-data attributes from a multi-frame image data object into the individual single-frame image data objects.

Figure 3:
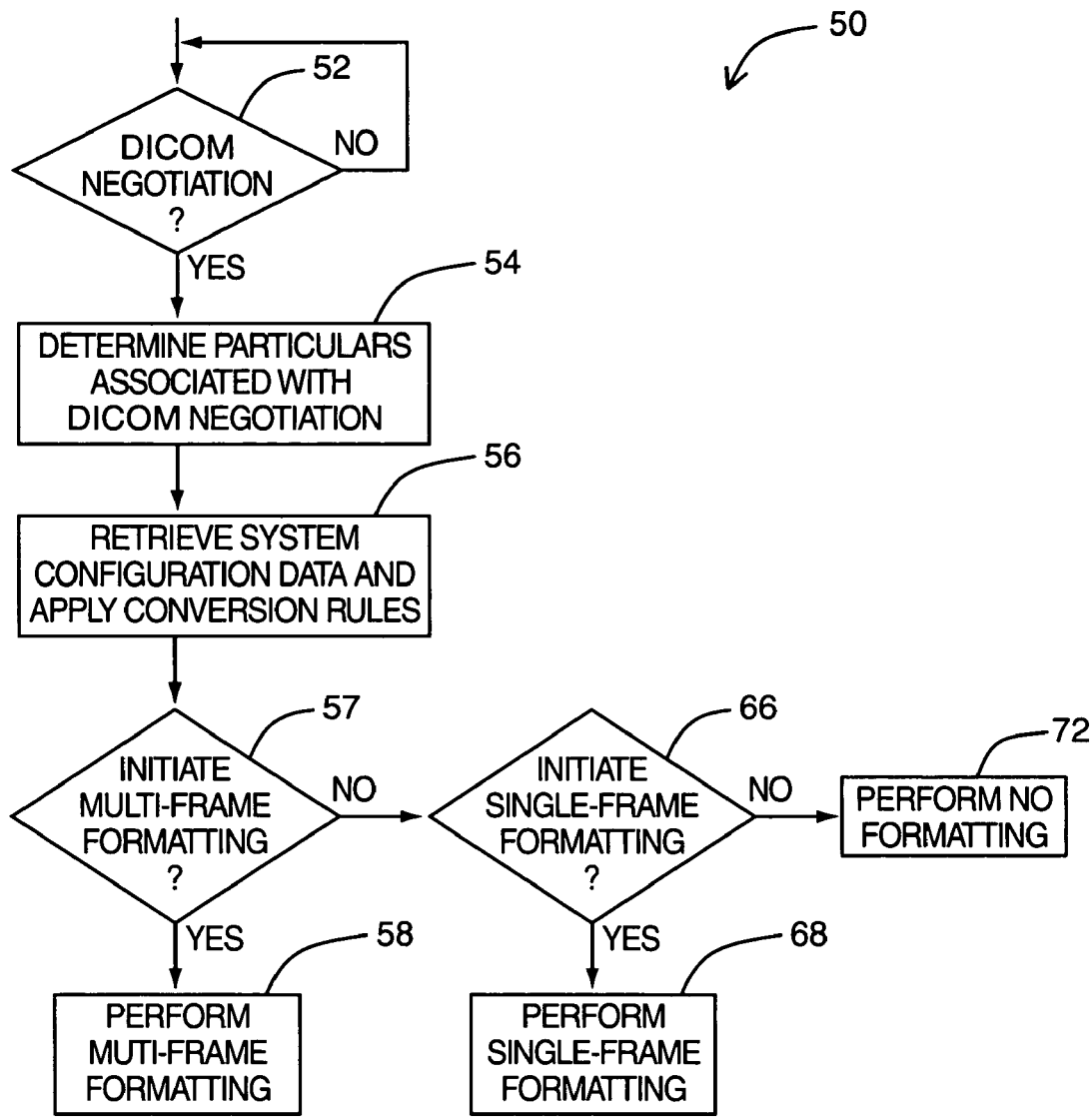
FIG. 3 is a flowchart illustrating the general operational steps of the exemplary embodiment of the image data conversion system of FIG. 1.

Referring now to FIGS. 1, 2, and 3, the general operation of the image data conversion system 10 will be discussed. In particular, FIG. 3 is a flowchart that illustrates the general operational steps 50 executed by image data conversion system 10. As discussed above, the conversion module 12 coordinates the operation of the tracking module 14, the multi-frame formatting module 16 and the single-frame formatting module 18 to interface the data formats utilized by imaging equipment that runs on old DICOM standards (e.g. old standard modality 13, the old standard image servers 15, and the old standard archive 17) and imaging equipment which operate under the new EMRCT standard (e.g. local PACS network(s) 20).

It should be understood that the new standard PACS 20B is configured to support both the old (single-frame) and the new (Enhanced Multi-Frame) image data object formats. However, other old standard DICOM devices such as the old standard PACS 20A or the old standard modality 13A only support the old single-frame image data object standard. Accordingly, when the new standard PACS 20B negotiates image data object transfer with an old standard DICOM device, they must agree on the Service-Object Pair (SOP) Class and the transfer syntax to be used.

Specifically, at step (52), the tracking module 14 is used to determine whether a DICOM negotiation (i.e. to agree on the SOP Class and transfer syntax) has been detected between new image manager/archive 28B and an external imaging equipment device. If not, then step (52) is repeated. As conventionally known, a DICOM association between imaging equipment includes a negotiation step where the requesting device will indicate which image data standards or formats it supports. For example, a requesting device will indicate that it supports the Enhanced Multi-Frame standard by providing the particular DICOM SOP Class identifiers for Enhanced Multi-Frame CT, MR or XA image data objects in association with the details of the requested image data object (e.g. a study, a series or an image, etc.).

If a DICOM negotiation has been detected by the tracking module 14, then at step (54), the conversion module 12 instructs the tracking module 14 to determine the particulars associated with the detected DICOM negotiation. The DICOM negotiation can be associated with various types of specific workflow requests including a storage or archival request (e.g. a CSTORE request), transmission request, import request, or export request. These particulars include image characteristics, study characteristics and workflow characteristics of the image data request.

Image characteristics of the image data request include image properties, bit depth etc. Study characteristics of the image data request include the type of modality, the source station ID, the body part, number of images within a series (if applicable). Workflow characteristics of the image data request include the source and destination of the image data request, the various data formats that the negotiating imaging equipment device supports, the agreed-upon SOP Class and transfer syntax etc.

Based on the detected DICOM negotiation particulars, at step (56), the conversion module 12 retrieves appropriate system configuration data and conversion rules from image conversion database 23 and determines whether image data conversion is necessary and if so whether the image data conversion should be multi-frame formatting or single-frame formatting. The specific types of configuration data and conversion rules that can be utilized will be discussed in more detail in relation to FIG. 5.

It should be understood that if the DICOM association has been made by the external imaging equipment device for the purposes of sending or storing image data to the new image manager/archive 28B, then the image data objects would be transmitted accordingly at this point.

If at step (57), the conversion module 12 determines whether multi-frame formatting is required and if so then at step (58), the conversion module 12 instructs the multi-frame formatting module 16 to perform multi-frame formatting on the single-frame image data objects at issue. The multi-frame formatting module 16 receives the single-frame image dataset (FIG. 2) that consists of a plurality of single-frame image data objects. As shown in FIG. 2, each single-frame image data object contains meta-data and pixel data. The multi-frame formatting module 16 performs multi-frame formatting on the received single-frame image dataset and generates an equivalent multi-frame image object (FIG. 2) as will be described in detail.

If not, then at step (66), the conversion module 12 determines whether single-frame formatting is required. If so, then at step (68), the conversion module 12 instructs single-frame formatting module 18 to perform single-frame formatting on the multi-frame image data object at issue. The single-frame formatting module 18 receives the multi-frame image object (FIG. 2). The multi-frame formatting module 18 performs single-frame formatting on the received multi-frame image data object (FIG. 2) and generates an equivalent set of single-frame image data objects (i.e. a single-frame dataset).

If not, then at step (72), the conversion module 12 determines that no image data formatting is required, and the conversion module 12 will not instruct either multi-frame formatting module 16 or single-frame formatting module 18 to conduct image data formatting.

It should be understood that if the DICOM association has been made by the external imaging equipment device for the purposes of requesting or retrieving stored image data from the new image manager/archive 28B, then the image data objects would be transmitted accordingly at this point.

Generally speaking, it should be understood that the DICOM negotiation dictates the correct format (if any) for transfer to or from the requesting device. For example, if an entire CT study is requested by an imaging equipment device and multi-frame CT is supported by the requesting device then multi-frame would most likely be used. If however, only a single CT study image is requested by an imaging equipment device that supports multi-frame CT then only a single-frame of the study would be returned. These kinds of efficiency determinations can be made based on the various BICOM negotiation particulars (e.g. SOP Class and transfer syntax, etc.) and configuration information and appropriately designed conversion rules stored in image conversion database 23.

Figure 4:
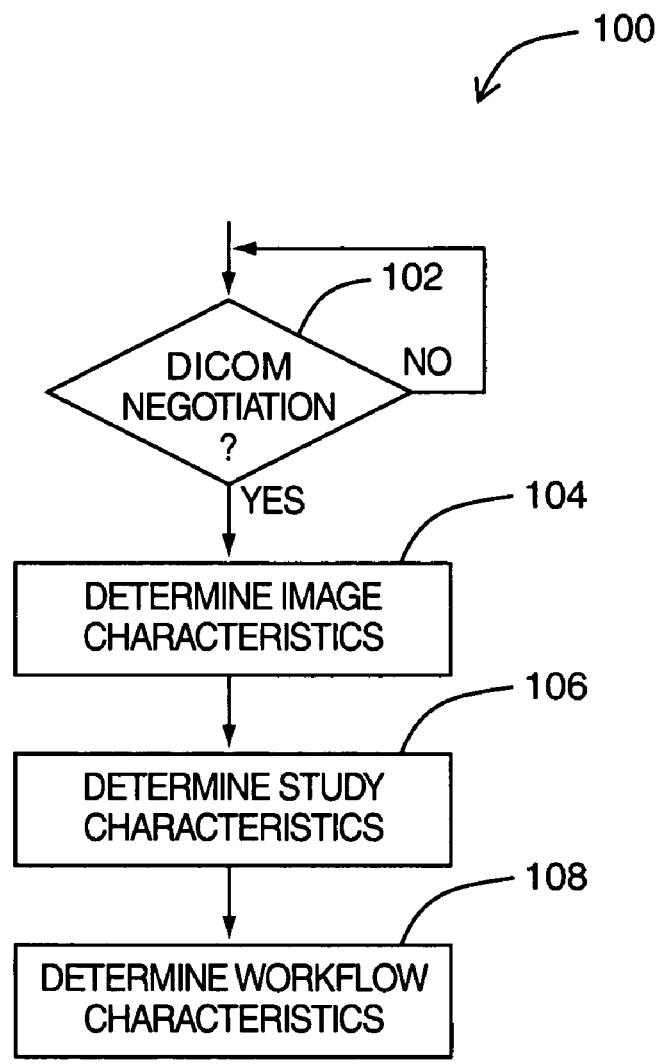
FIG. 4 is a flowchart illustrating the operational steps of the tracking module of FIG. 1.

Referring now to FIGS. 1, 2, 3, and 4, the general operation of the image data conversion system 10 will be discussed. In particular FIG. 4 is a flowchart that illustrates the general operational steps 100 executed by the tracking module 14.

At step (102), the tracking module 14 detects a DICOM negotiation between the new standard PACS 20B and an external imaging equipment device. As previously discussed, the DICOM negotiation is associated with a specific imaging workflow event such as a storage/archival request, a transmission request, an export request or import image data request.

At step (104), the tracking module 14 determines various image characteristics associated with the image data request. As previously discussed, image characteristics of the image data request include image properties, bit depth etc.

At step (106), the tracking module 14 determines various study characteristics associated with the image data request. As discussed, study characteristics of the image data request include the type of modality, the source station ID, the body part, number of images within a series (if applicable).

At step (108), the tracking module 14 determines various workflow characteristics of the image data request including the source and destination of the image data request, the various data formats that the negotiating imaging equipment device supports, the agreed-upon SOP Class and transfer syntax etc.

Figure 5:
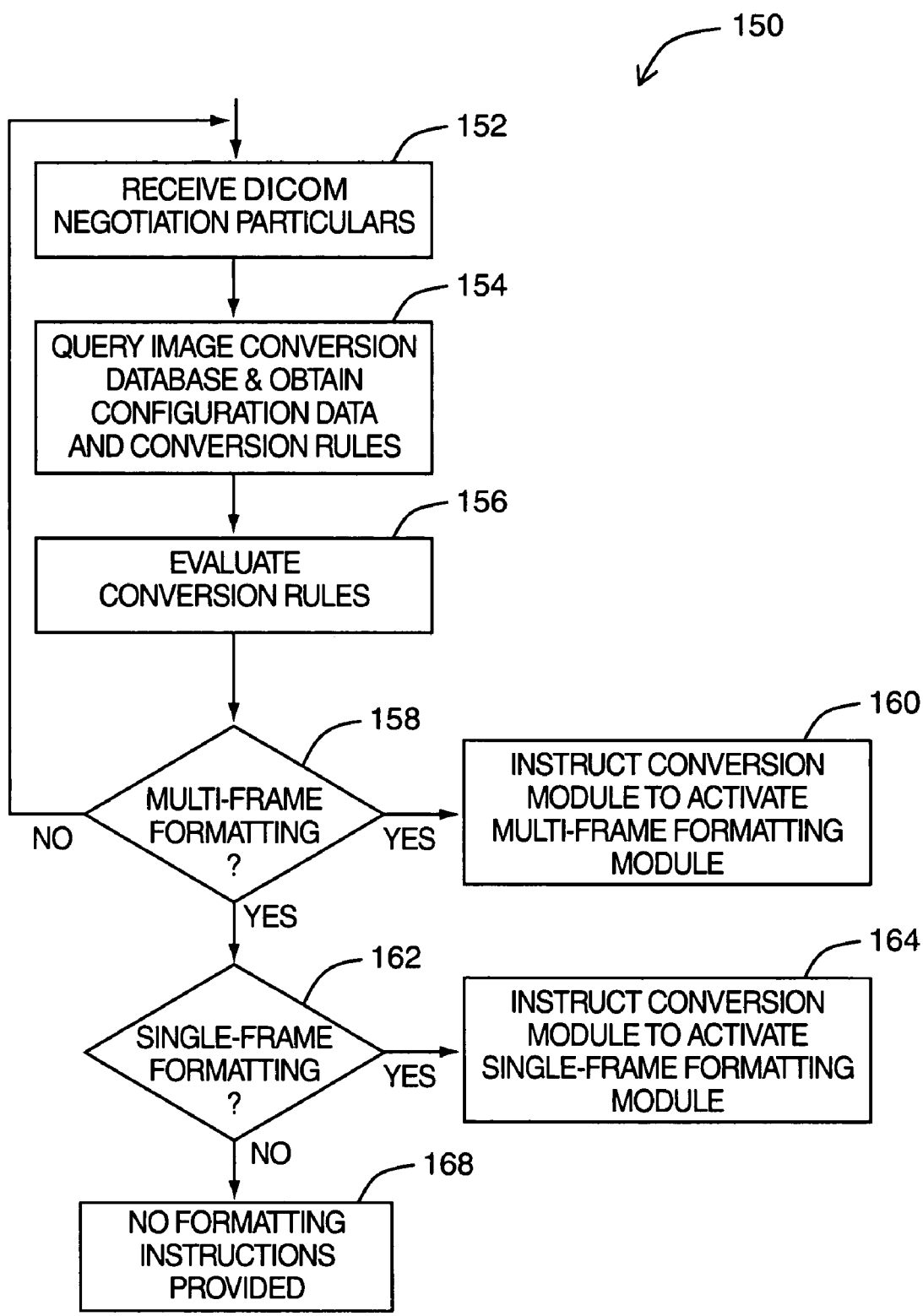
FIG. 5 is a flowchart illustrating the operational steps of the conversion module of FIG. 1.

Referring now to FIGS. 1, 2, 3, and 5, further general operation of the image data conversion system 10 will be discussed. In particular FIG. 5 is a flowchart that illustrates the general operational steps 150 executed by the conversion module 12.

At step (152), the conversion module 12 receives the various DICOM negotiation particulars (i.e. the image, study and workflow characteristics discussed above) as determined by the tracking module 14. As discussed, these negotiation particulars include the various data formats that the various negotiating imaging equipment devices support. The tracking module 14 provides this information to the conversion module 12.

At step (154), the conversion module 12 queries the image conversion database 23 to determine system configuration data that relates to the relevant DICOM negotiation particulars (e.g. available bandwidth, overall image data file sizes, estimated download time, etc.) and which will have a bearing on the determination on whether to perform multi-frame format, single-frame format or not. The conversion module 12 also queries the image conversion database 23 to obtain relevant conversion rules for application to the relevant negotiation particulars (i.e. image, study and workflow characteristics) and system configuration data.

At step (156), the conversion module 12 evaluates the conversion rules using the negotiation particulars (e.g. the image, study and workflow characteristics discussed above) and the related configuration data (e.g. available bandwidth, overall image data file sizes, estimated download time, etc.) As discussed above, the conversion rules are designed to allow for an effective determination of whether multi-frame formatting, single-frame formatting or none should be applied to a particular set of image data objects.

At step (158), the conversion module 12 determines whether multi-frame formatting is appropriate. If so, then at step (160), the conversion module 12 instructs the multi-frame formatting module to conduct multi-frame formatting on the relevant single-frame image data objects.

At step (162), the conversion module 12 determines whether single-frame formatting is appropriate. If so, then at step (164), the conversion module 12 instructs the single-frame formatting module to conduct single-frame formatting on the relevant multi-frame image data objects.

Finally, if it is determined that neither multi-frame nor single-frame formatting is required then it is determined at step (168) that no formatting instructions are required.

Figure 6:
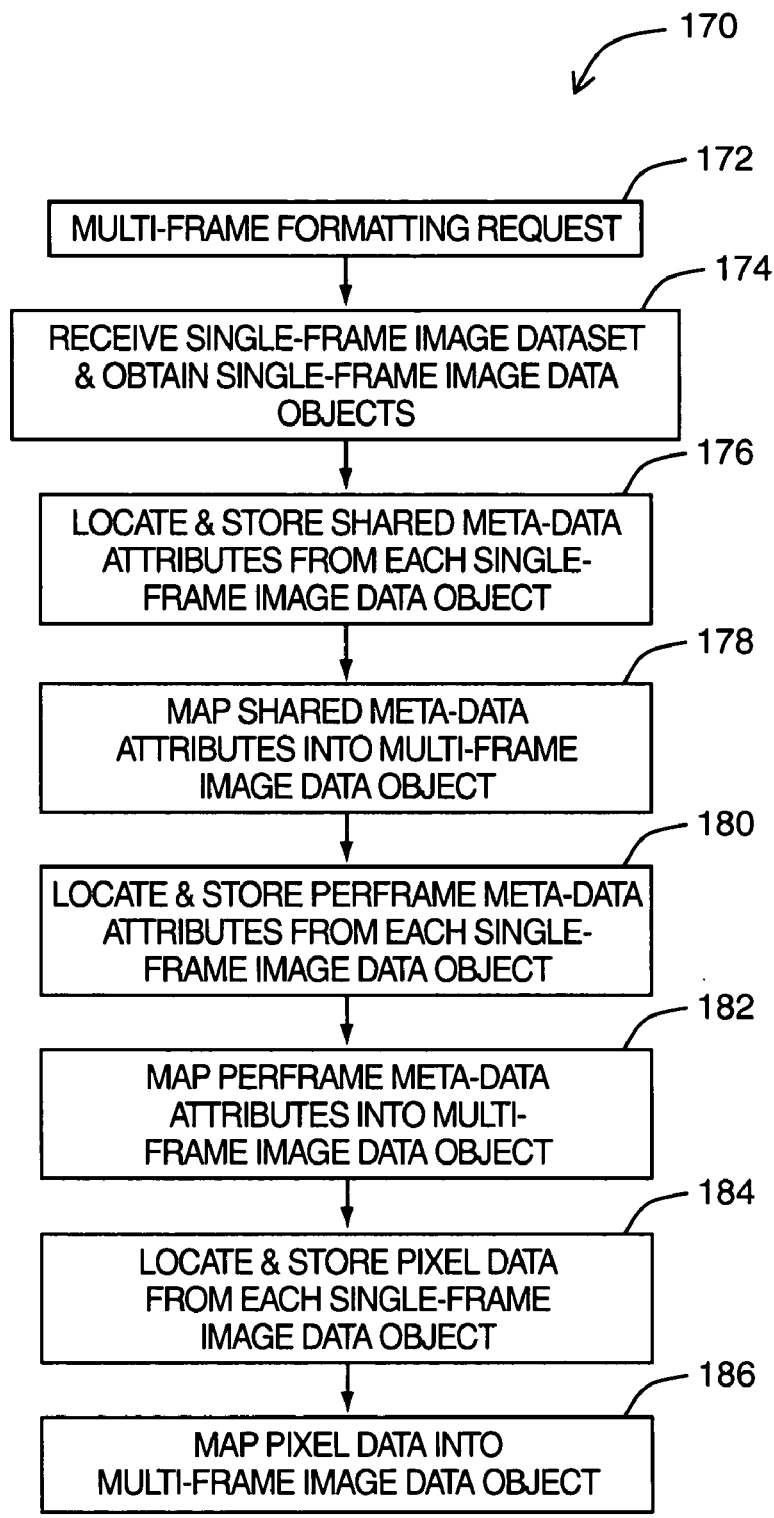
FIG. 6 is a flowchart illustrating the operational steps of the multi-frame formatting module of FIG. 1.

Referring now to FIGS. 1, 2, 3, and 6, further operation of the image data conversion system 10 will be discussed. In particular FIG. 6 is a flowchart that illustrates the general operational steps 170 executed by the multi-frame formatting module 16. The multi-frame formatting module 16 is used to convert a plurality of single-frame image data objects within a single-frame image dataset into a multi-frame image data object.

At step (172), the conversion module 12 instructs multi-frame formatting module 16 to perform multi-frame formatting on the single-frame image dataset after receipt of the single-frame image data objects by the network gateway 22B.

At step (174), the multi-frame formatting module 16 receives the single-frame image dataset. The multi-frame formatting module 16 then obtains the complete set of single-frame image data objects from the single-frame image dataset. As an illustration of this step, as shown in FIG. 2, the three single-frame image data objects shown at the left of the figure would be identified by the multi-frame formatting module 16.

At step (176), the multi-frame formatting module 16 locates and stores shared meta-data attributes from each single-frame image data object. Referring back to the example, the three single-frame image data objects shown in FIG. 2, namely Frame A, Frame B and Frame C each have the same following meta-data attributes in common (i.e. shared attributes): Patientname ("John Doe"), FrameOfReference UID ("1.2.3.4.5"), and ImageOrientation ("AXIAL"). These three meta-data attributes would be considered to be shared meta-data attributes.

At step (178), the multi-frame formatting module 16 maps the shared meta-data attributes together as one set of shared meta-data attributes within the multi-frame image data object (FIG. 2). In this way, the overall storage size of the multi-frame image object will be significantly smaller than the equivalent single-frame image dataset since the redundancy previously created by repeated instances of shared meta-data attributes within the single-frame image objects has been eliminated.

At step (180), the multi-frame formatting module 16 locates and stores perframe meta-data attributes from each single-frame image data object. Referring back to the example, the three single-frame image data objects shown in FIG. 2, namely Frame A, Frame B and Frame C each have the same following meta-data attribute which is not in common (i.e. perframe attributes): SliceLocation ("1.0" for Frame A, "2.0" for Frame B, "3.0" for Frame C). This meta-data attributes would be considered to be a preframe meta-data attribute.

At step (182), the multi-frame formatting module 16 maps the perframe meta-data attributes individually into the multi-frame image data object. That is as shown in FIG. 2, three separate perframe attributes are provided, one for each Frame.

At step (184), the multi-frame formatting module 16 locates and stores pixel data from each single-frame image data object. Referring back to the example, the three single-frame image data objects shown in FIG. 2, namely Frame A, Frame B and Frame C each have their own pixel data, namely Pixel Data A, Pixel Data B, Pixel Data C.

Finally, at step (186), the multi-frame formatting module 16 maps the pixel data individually into the multi-frame image data object. That is as shown in FIG. 2, three separate pixel data entities are provided, one for each Frame.

Figure 7:
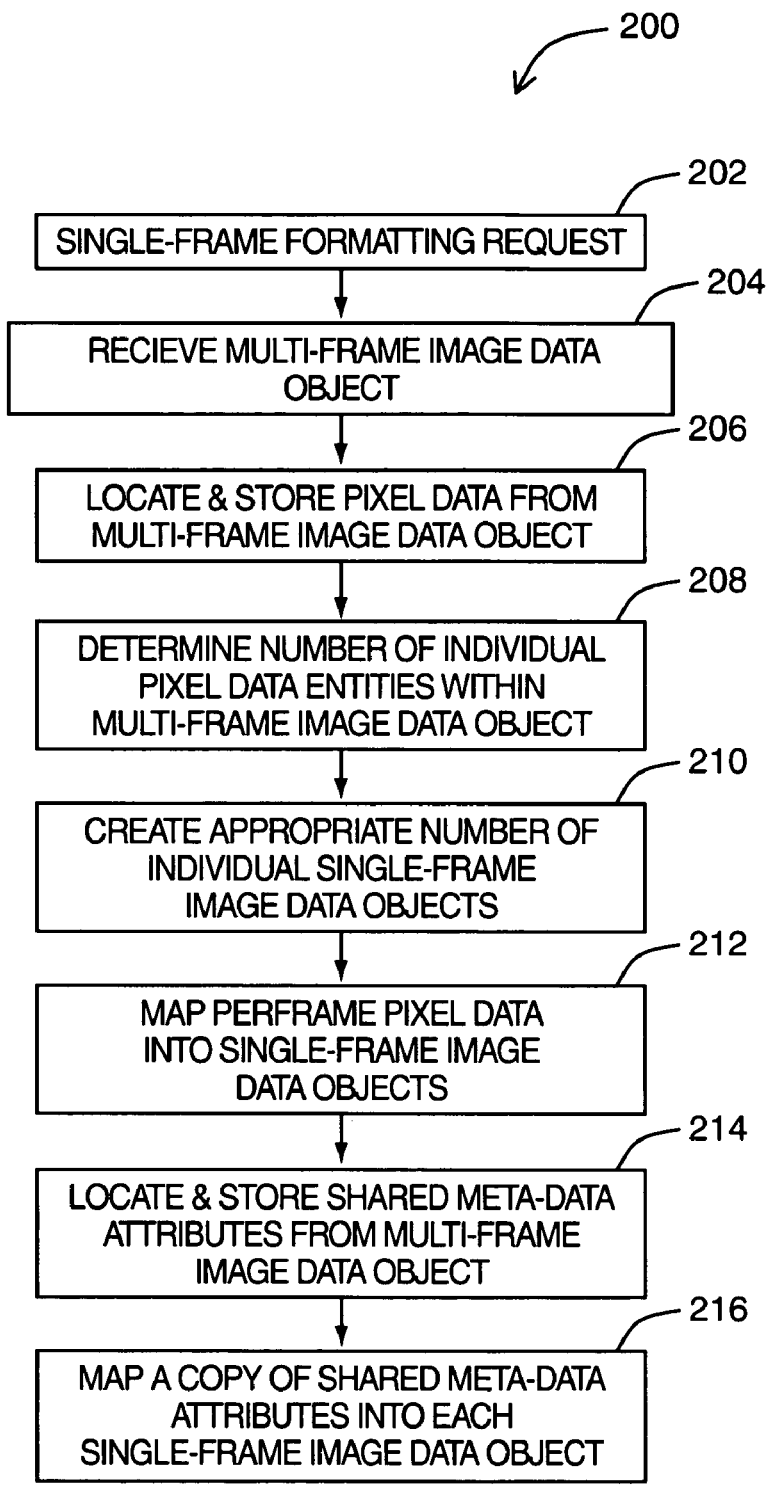
FIG. 7 is a flowchart illustrating the operational steps of the single-frame formatting module of FIG. 1.

Referring now to FIGS. 1, 2, 3, and 7, further general operation of the image data conversion system 10 will be discussed. In particular FIG. 7 is a flowchart that illustrates the general operational steps 200 executed by the single-frame formatting module 18. The single-frame formatting module 18 is used to convert a multi-frame image data object into an appropriate number of single-frame image data object.

At step (202), the conversion module 12 requests that single-frame formatting module 18 perform single-frame formatting on a multi-frame image data object (FIG. 2).

At step (204), the single-frame formatting module 18 receives the multi-frame image data object from the conversion module 12 that has intercepted it on its transmission path from source to destination. At step (206), the single-frame formatting module 18 locates and stores all of the individual pixel data entities from the multi-frame image data object. For example, referring again to FIG. 2, the single-frame formatting module 18 would store the individual pixel data entities shown, namely Pixel Data A, Pixel Data B, Pixel Data C.

At step (208), the single-frame formatting module 18 determines the number of individual pixel data entities within the multi-frame image data object. At step (210), the single-frame formatting module 18 then creates an appropriate number of individual single-frame image data objects that correspond to the number of individual pixel data entities. Again, the example shown in FIG. 2, it would be determined that there are three individual pixel data entities and accordingly, three separate single-frame image data objects are created.

At step (212), the perframe and pixel data, which are all individually represented within the multi-frame image data object, are then mapped into the individual single-frame image data objects. In the example shown in FIG. 2, the perframe meta-data attributes, namely "SliceLocation="1.0" (Frame A), "SliceLocation="2.0" (Frame B), and "SliceLocation="3.0" (Frame C) and the pixel data, namely Pixel Data A, Pixel Data B, and Pixel data C would be mapped into the individual single-frame image data objects shown at the right.

At step (214), the single-frame formatting module 18 locates and stores the shared meta-data attributes from the multi-frame object. At step (216), the shared meta-data attributes are then copies and mapped into each single-frame image data object. In the example, Frame A, Frame B and Frame C each have the same following meta-data attributes in common (i.e. shared attributes): Patientname ("John Doe"), FrameOfReference UID ("1.2.3.4.5"), and ImageOrientation ("AXIAL"). Three copies of these shared meta-data attributes would be made and then mapped into each of the three single-frame image data objects.

As an illustration of the general operation of image conversion system 10, various image workflow scenarios and the operation of image conversion system 10 will now be discussed.

As a first exemplary image workflow scenario, the old standard modality 13A initiates a DICOM association with the new standard network gateway 22B of the new image manager/archive 28B, to CSTORE it's single-frame CT images. As discussed, a DICOM negotiation ensues where the old standard modality 13A and the new standard network gateway 22B determine the SOP Class and transfer syntax. As previously discussed, the new standard PACS 20B is configured to support both the old (single-frame) and the new (Enhanced Multi-Frame) image data object formats so the new standard network gateway 22B could accept either from an external device. At step (52), the tracking module 14 detects this DICOM negotiation. The old standard modality 13A then transfers, for example, 2000 single-frame image data objects all associated with a study. After transfer the old standard modality 13A closes the DICOM association with the new image manager/archive 28B.

Since the tracking module 14 has detected the DICOM negotiation, at step (54), the tracking module 14 determines the particulars associated with the DICOM negotiation. At step (56), the conversion module 12 retrieves the relevant system configuration data and conversion rules from image conversion database 23 and applies certain conversion rules to determine whether to initiate multi-frame formatting, single-frame formatting or neither. In this case, one exemplary conversion rule could be that if the modality type is CT and if there are over 500 single-frame instances then multi-frame formatting should be instigated. Since these conditions have been met, at step (57), conversion module 12 would instruct multi-frame formatting module 16 to initiate multi-frame formatting of the 2000 single-frame image data objects for the study at issue for storage in the storage module 24B (i.e. cache).

Then subsequent to the multi-frame formatting, tracking module 14 continues to, at step (52), monitor for DICOM negotiations. If at step (52), tracking module 14 detects that a DICOM negotiation associated with a request (e.g. a CGET request) by new standard user workstation 19B for this particular study, then at step (54) the tracking module 14 determines particulars associated with this DICOM negotiation including the fact that the requesting imaging equipment is the new standard user workstation 19B that operates according to the Enhanced Multi-Frame standard. At step (56), the conversion module 12 retrieves relevant system configuration data and conversion rules and determines whether multi-frame, single-frame or no formatting is required. In this case, since the study at issue is already in multi-frame format, this multi-frame image data will simply be transferred from the new image manager/archive 28B to the new standard user workstation 19B as a multi-frame CT image data object.

Alternately, it should be understood that in the above-noted scenario, in the case where the old standard modality 13A negotiates to transfer 200 single-frame CT image data objects to the network gateway 22B, application of the relevant conversion rules at step (58) would indicate that no formatting would be required at step (72) due to the small number of single-frame objects which could be multi-frame formatting subsequently without much delay. Accordingly, the new image manager/archive 28B would simply store the 200 single-frame CT image data objects in their original (i.e. old single-frame standard) format within storage module 24B.

Then subsequently, if the new image manager/archive 28B receives requests from a new standard device (e.g. the new standard user workstation 19) will then apply multi-frame formatting to the single-frame image objects for transmission or export. If instead, the new image manager/archive 28B receives a request from an old standard device (e.g. the old image manager/archive 28A of the old standard PACS 20A) then the old standard single-frame image objects will be transmitted or exported directly.

As illustrated above, it should be understood that image data conversion system 10 is designed to accommodate the fundamental timing differences between multi-frame formatting and single-frame formatting. The multi-frame formatting process is inherently slow due to the typically large number of images that need to be processed. Accordingly, image conversion system 10 is adapted to perform anticipatory multi-frame formatting of single-frame image data in appropriate situations. This is accomplished using appropriately configured conversion rules such as the discussed conversion rule that indicates that multi-frame formatting be conducted when there are more than 500 single-frame CT image data objects at issue. Since multi-frame formatting is conducted directly as a result of a storage request that meets the requirements of the conversion rule, the multi-frame image data object is then available for efficient transmission in response to a subsequent retrieval request by multi-frame standard imaging equipment such as the new standard user workstation 19B.

In another illustrative imaging workflow scenario, the new standard modality 13B engages in a DICOM association with new standard image manager/archive 28B and requests a CSTORE of a multi-frame study. Consequently, the new standard modality 13B negotiates transfer of the multi-frame CT image data objects associated with this study with the new standard image archive 28B. The new standard modality 13B transfers the multi-frame object to the new standard image manager/archive 28B.

Accordingly, at step (52), the associated DICOM negotiation is detected and at step (54) the relevant particulars associated are determined and provided to conversion module 12. The conversion module 12 then retrieves system configuration data and applicable conversion rules and applies these conversion rules. The conversion module 12 determines that it is not worthwhile, according to the various applicable conversion rules, to perform single-frame formatting on this multi-frame image data object. As discussed above, generally speaking it is not worthwhile conducting single-frame formatting in advance of a subsequent request for the single-frame image data objects since single-frame formatting can effectively be performed "on the fly". Accordingly, the conversion module 12 determines at step (72) not to perform any formatting.

Subsequently, the old image manager 13A creates a DICOM association with the new image manager/archive 28B for a CMOVE of the study and negotiates a transfer using the single-frame CT image object format. The study at issue resides in the storage module 24B as a multi-frame image data object. At step (52), tracking module 14 detects this DICOM negotiation and then at step (54) identifies the necessary particulars associated with the DICOM negotiation. At step (56), the conversion module 12 retrieves relevant system configuration and conversion rules from the image conversion database 23 and determines that single-frame formatting is necessary. The conversion module 12 then instructs the single-frame formatting module 18 to conduct single-frame formatting to convert the multi-frame image data object to single frame image data objects "on the fly" and sent to the old image manager 13A.

Another typical imaging workflow scenario is where single-frame image data objects (i.e. a single-frame image dataset) is generated by the old standard modality 13A and it is desired to store this image data within the storage module 24B using an archive request. The archive request would require that the image data be transmitted from the old standard image data archive 17 to the local PACS network 20 and the associated DICOM negotiation would be detected by tracking module 14 at step (52). Then, depending on the specific particulars associated with the DICOM negotiation determined at step (54), along with the configuration data and the conversion rules retrieved at step (56) the conversion module 12 determines the specific formatting (if any) to be performed. The old standard modality 13A then transmits the image data objects to the network gateway 22B and any applicable formatting (if any) as determined above is performed and the image data objects are stored for future access within the new standard PACS 20B.

Another typical imaging workflow scenario is a meta-data update. That is, where meta-data for a particular multi-frame image data object or study has been requested to be updated by an external Radiology Information System (RIS) 29 (FIG. 1). As conventionally known, HL7 is the protocol utilized by RIS 29 and admission, discharge and transfer (ADT) information is maintained. Generally speaking, new image manager/archive 28B support HL7 transactions in addition to DICOM transactions and tracking module 14 is adapted to recognize HL7 transactions along with DICOM transactions.

Specifically, when the RIS 29 requests to overwrite the equivalent single-frame image dataset stored within the new standard storage module 24B, the HL7 ADT update patient information message is identified by tracking module 14. Then the specific applicable formatting is determined by conversion module 12 according to the HL7-related negotiation particulars determined at step (54) and the system configuration data and conversion rules determined at step (56). The details of the amendments are contained within the HL7 ADT update patient information message. Accordingly, the details of the meta-data update are obtained from the HL7 ADT message and the image manger's storage module 24B within the new PACS 20B is updated appropriately.

Typically, the new standard PACS 20B would make the change to the study by changing the data in the database, applying those changes when the image data is transmitted or exported. (i.e. in the cache on disk) is not altered once received for patient data regulatory requirements. Also, typically only changes to the dataset would be provided to affect an update. In the situation where pixel data is not altered only the changes (usually in annotations or image enhancement settings etc.) are used to update the data within storage module 24B. The new standard PACS 20B then makes changes to the study by changing the data in the database, applying those changes when the image data is transmitted or exported.

Now referring to FIGS. 1, 2, 3 and 8A, 8B and 8C, the operation of image data conversion system 10 in the context of what is conventionally known as "soft splitting" and "hard splitting" study segmentation will be discussed.

Figure 8A:
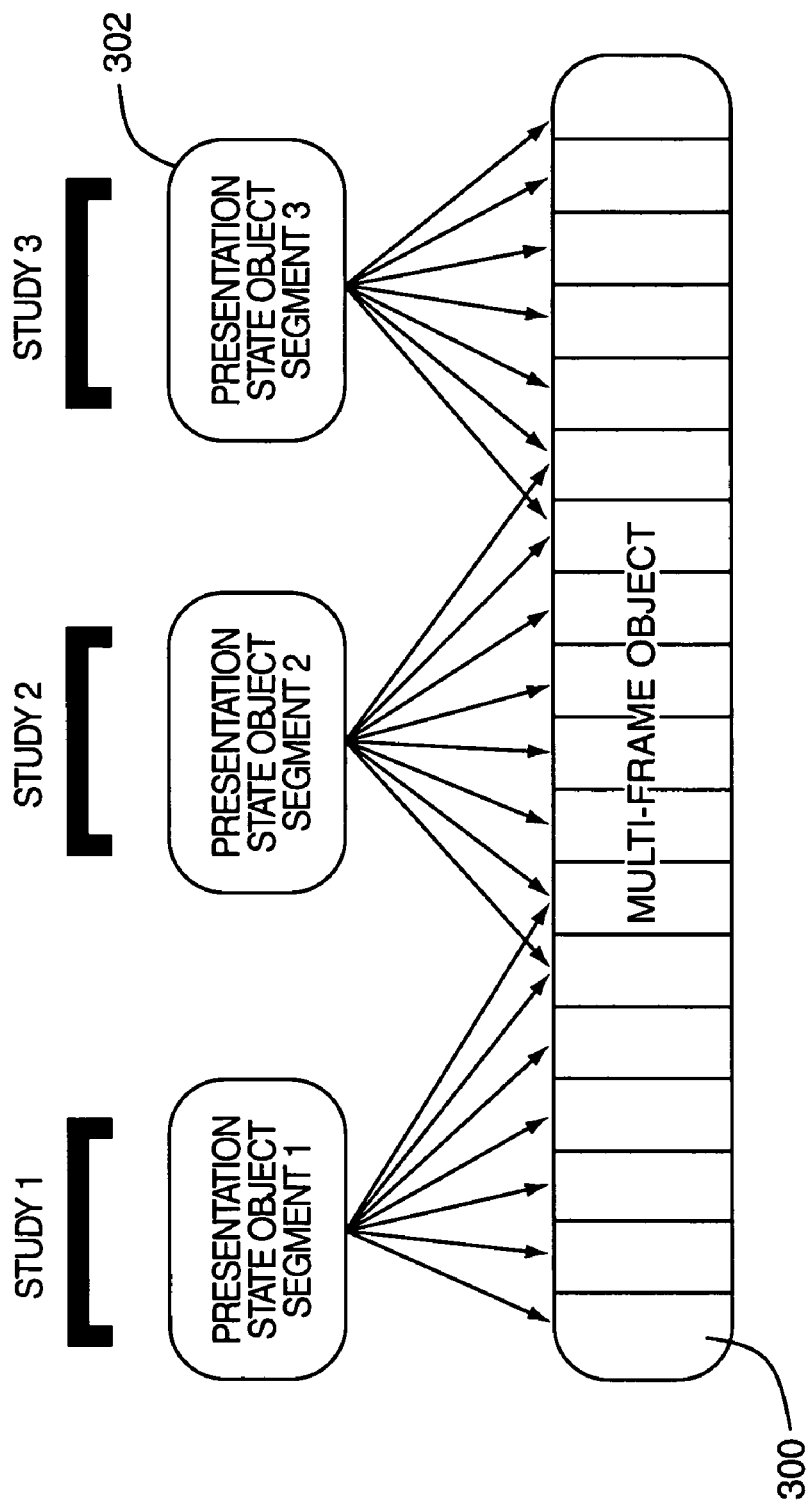
FIGS. 8A, 8B and 8C are schematic diagrams that illustrate soft and hard splitting techniques utilized by the image data conversion system of FIG. 1.

FIG. 8A illustrates what is conventionally known as "soft splitting". "Soft splitting" refers to the splitting of a multi-frame image data object or study 300 into multiple segments (i.e. new studies) where a new DICOM object 302 is created for each segment. Each of these objects are created to reference the related frames, and specifically, to reference a DICOM presentation state object. With "soft splitting", no new image objects are created.

Figure 8B:
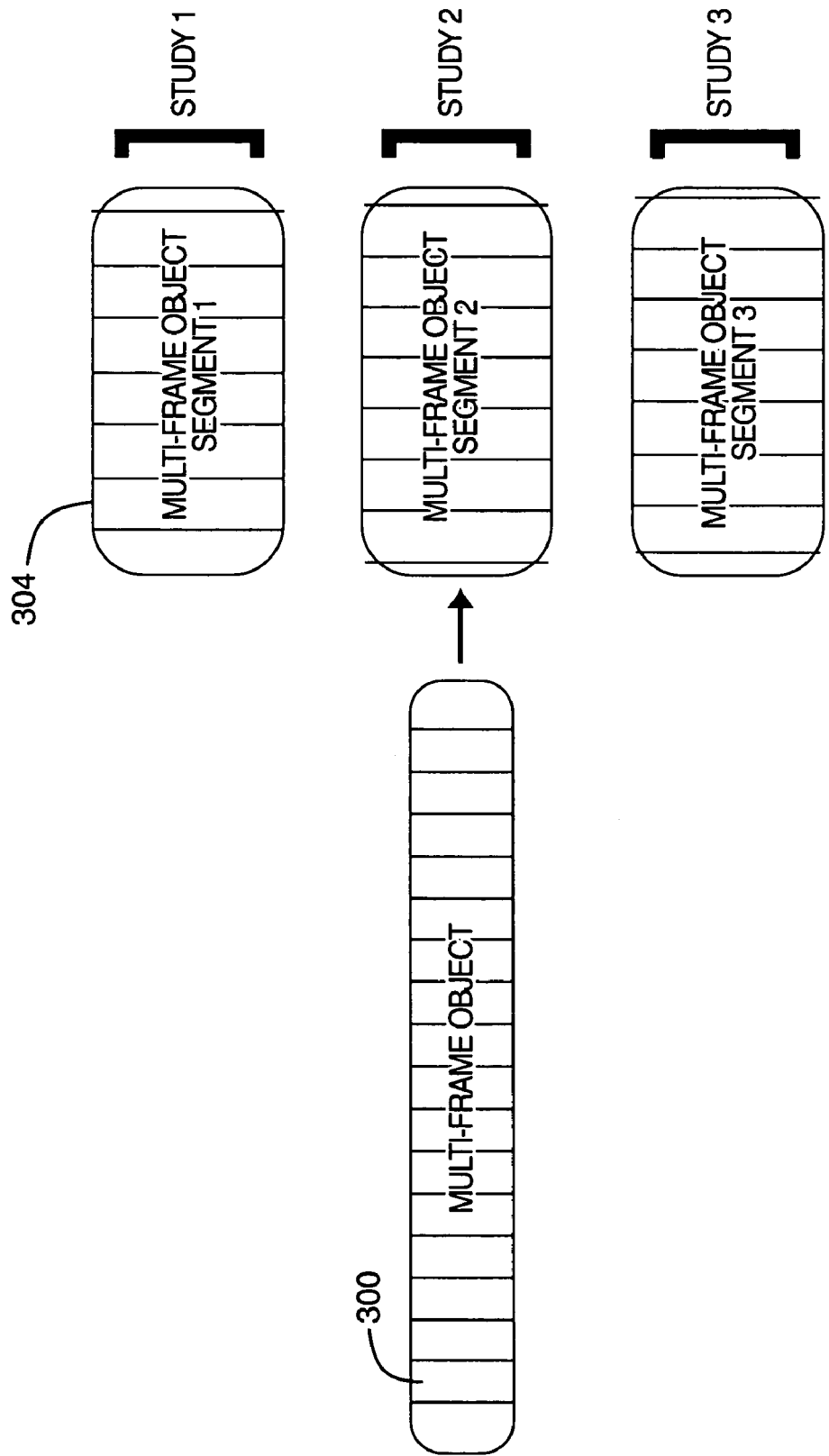

FIG. 8B illustrates what is conventionally known as "hard splitting". "Hard splitting" refers to the splitting of a multi-frame image data object or study 300 into multiple segments where a new multi-frame object 304 is created for each segment. As shown, with "hard splitting", new multi-frame image data objects are created.

Figure 8C:
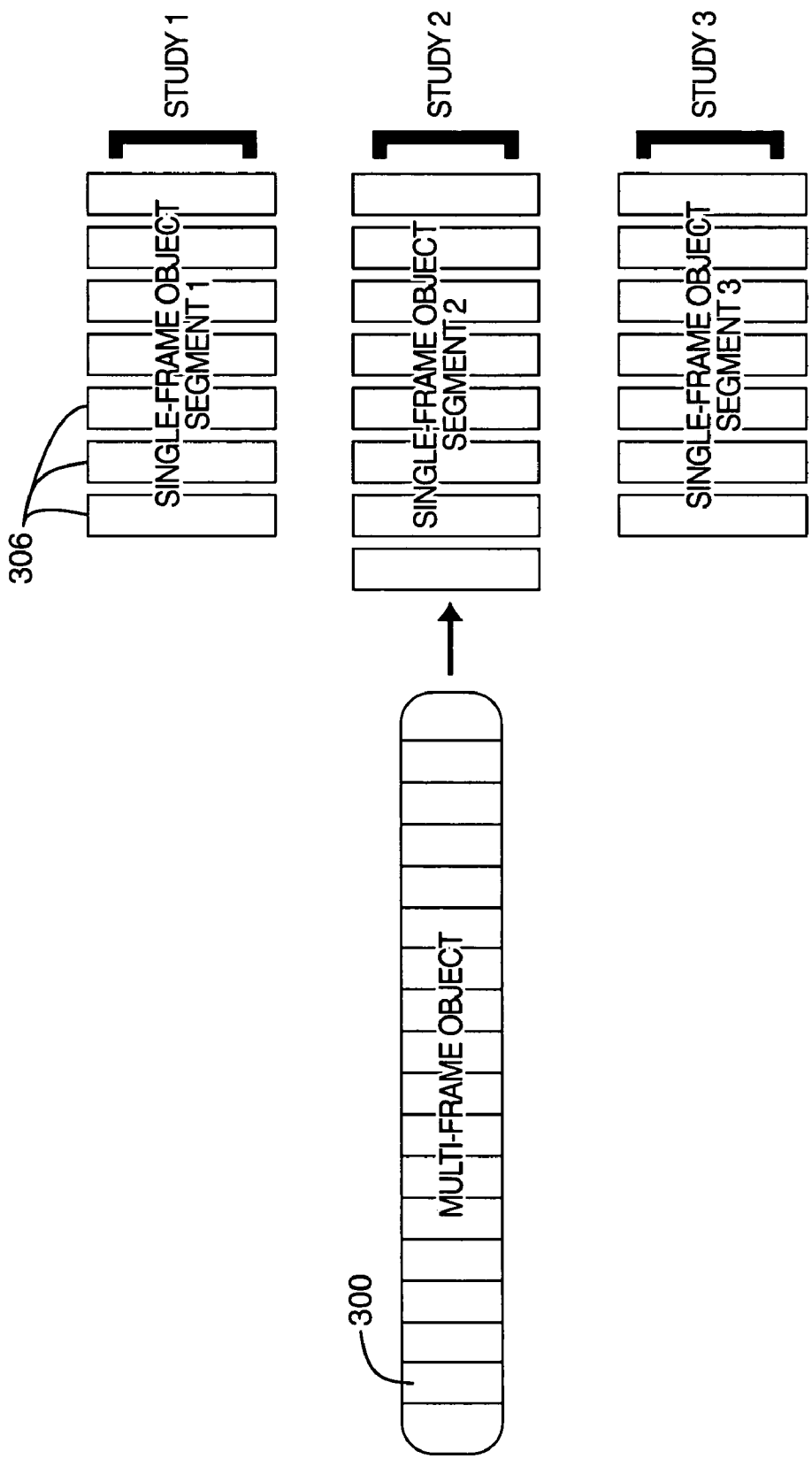

FIG. 8C illustrates the application of the single-frame formatting that can be performed on a multi-frame image data object or study 300 by image data conversion system 10 as discussed above. As previously discussed, single-frame formatting is applied to a multi-frame image data object 300 and produces a plurality of single-frame image data objects 306 which can grouped into study segments as shown in FIG. 8C.

In the case of multi-frame objects, there is current support in the existing DICOM specification for "soft splitting" Enhanced Multi-Frame image data objects. That is, references to frame numbers are supported for presentation state objects as between new standard imaging equipment devices. If, for example, a first new standard imaging equipment device requests presentation state object #1 (FIG. 8A) from a second new standard imaging equipment device, the second imaging equipment device would simply transmit the multi-frame image data object (FIG. 8A) along with the frame number references associated with the presentation state object #1 back to the requesting device.

However, in the case where "soft splitting" is used internally within a new standard PACS 20B to represent a segmented study and where it is desired to support transmission and receipt from old standard imaging equipment as in the present case, the new standard PACS 20B would still be required to support "hard splitting" on export to an old standard imaging equipment device (i.e. that only supports the old standard single-frame DICOM format). It is necessary for the new standard PACS 20B to support "hard splitting" in such a scenario, in order to limit the amount of data delivered to the old standard external imaging equipment device requesting export.

For example, if an old standard workstation 19A requests study #2 that is contained within an entire multi-frame image data object (FIG. 8C) stored on new standard PACS 20B, it is necessary for the new standard PACS 20B to create single-frame segment(s) that contain only the requested single-frame image data for the requested study for export.

Further, even if new standard user workstation 19B requests a study, for example study #3 that is contained within an entire multi-frame image data object (FIG. 8B) stored on new standard PACS 20B, it is not efficient to return the entire multi-frame image data object with a single presentation state object that references the relevant slices for segment #3 back to the old standard workstation 19A. Rather, it would be necessary for the new standard PACS 20B to create multi-frame segment(s) that contain only the requested image data for the requested study for export.

Figure 9:
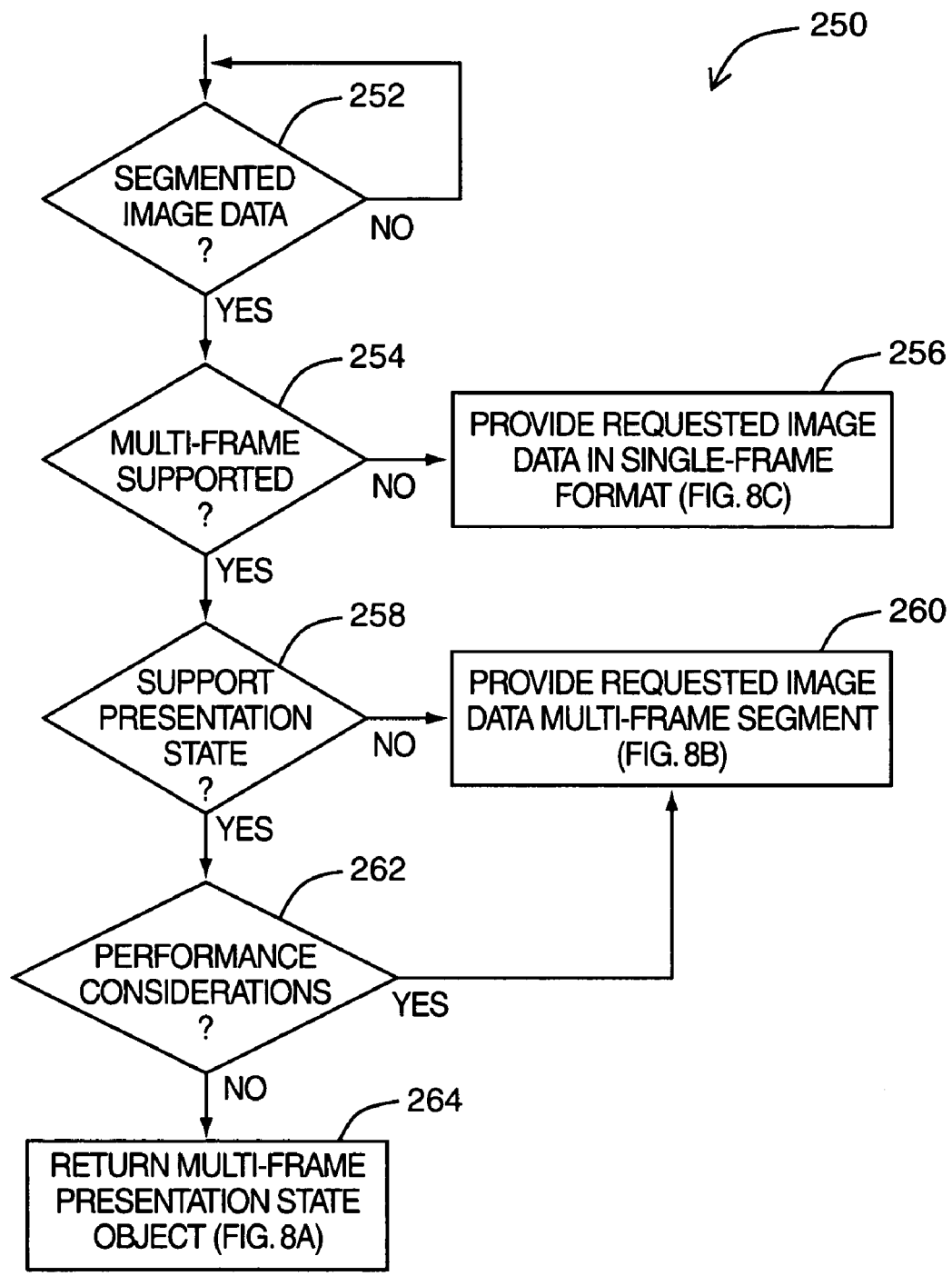
FIG. 9 is a flowchart illustrating the operational steps of the image data conversion system of FIG. 1 used to accommodate soft splitting within a multi-frame image data object.

Accordingly, reference is made to FIGS. 8A, 8B, 8C and 9, where FIG. 9 illustrates the operational steps 250 of the image data conversion system 10 when a request for segmented image data has been received.

Specifically, at step (252), it is determined whether the network gateway 22B of new image manager/archive 28B has received a request for segmented image data. If so, then the format and extent of the retrieved image data will depend on whether the request has originated from new standard imaging equipment or old standard imaging equipment and on performance factors such as the projected conversion time (i.e. based on image data object(s) size and available bandwidth, etc.)

At step (254), the conversion module 12 determines whether the requesting imaging equipment supports the new multi-frame standard. If not and rather the requesting imaging equipment supports only the single-frame standard, then at step (256), the conversion module 12 retrieves and provides the requested image data objects in single-frame format as shown in FIG. 8C. Namely, the single-frame image data objects associated with study #1, or #2, or #3, or a combination, as requested. In the example discussed above, the single-frame image data objects associated with study #2 would be provided. In one embodiment, the single-frame formatting module 18 would be adapted to ensure that the requested segments are generated (on the fly) as single-frame image data objects for export and that these single-frame image data objects contain only the requested images for the requested study.

If the requesting imaging equipment supports the new multi-frame standard, then at step (258), the conversion module 12 determines whether the requesting imaging equipment supports presentation state objects.

If not, then at step (260), the conversion module 12 retrieves and provides the requested "hard-split" image data multi-frame segment as shown in FIG. 8B. In the example discussed above, the multi-frame image data object segment associated with study #3 would be retrieved and provided.

If the requesting imaging equipment supports presentation state objects, then at step (262) conversion module 12 determines various performance factors such as the projected conversion time (i.e. based on image data object(s) size and available bandwidth, etc.) If there are not any performance considerations (i.e. if appreciable conversion delays are not predicted) then at step (264) the conversion module 12 provides the requested multi-frame presentation state object (e.g. #1 as discussed in the example above) as shown in FIG. 8A. As discussed above, this involves receiving and providing the multi-frame image data object along with relevant frame numbers to identify the requested presentation state object(s).

If there are performance considerations, then at step (260), the conversion module 12 retrieves and provides the requested "hard-split" image data multi-frame segment as shown in FIG. 8B in order to avoid predicted conversion time delays. In the example discussed above, the multi-frame image data object segment associated with study #3 would be retrieved and provided.

It should be understood that while the image data conversion system 10 has been described in the context of an old standard modality 13A, old standard PACS 20A, new standard modality 13B, new standard user workstation 19, and a new standard PACS 20B, the image data conversion system 10 would of course be equally applicable to new standard modalities, new standard image servers, new standard image data archives and old standard local PACS networks or for that matter, any combination of new and old standard imaging equipment.

In addition, it should be understood that while the image data conversion system 10 has been described in the context of a system that is able to manage the data transfer between one set of equipment that runs on the old DICOM image data standard and other set of equipment that runs on the newer DICOM Enhanced Multi-Frame image data standard, image data conversion system 10 could be used to manage the data transfer between equipment that supports any two different types of image data standards.

It will be appreciated that while image display system 10 has been described in the context of medical image management in order to provide an application-specific illustration, it should be understood that image display system 10 could also be applied to any other type of image or document display system. The system, processes and methods described are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

It should be understood that various modifications can be made to the embodiments described and illustrated herein, without departing from the embodiments, the general scope of which is defined in the appended claims.

The invention claimed is:

1. A system for storing image data objects and for retrieving the image data objects, the system comprising:
   a memory for storing imaging data objects, each image data object being stored in a single-frame image data standard or a multi-frame image data standard; and
   a processor coupled to the memory configured to:
      detect a data transmission negotiation from an external imaging device for a workflow request for one or more requested image data objects;
      when a data transmission negotiation is detected, determine a first set of negotiations particulars of the negotiation, the first set of negotiation particulars comprising an indication of the image data standard supported by the external imaging device and an indication of a type of workflow request;
      determine whether to convert the one or more requested image data objects based on the first set of negotiation particulars; and
      if the requested image data objects is to be converted, determining whether to convert the requested image data objects to the single-frame image data standard or the multi-frame image data standard;
   wherein the external imaging device supports at least one of the single-frame image data standard or the multi-frame image data standard;
   wherein the workflow request type is a retrieve type for retrieving one or more requested image data objects from the memory or a store type for storing one or more requested image data objects to the memory;
   wherein each single-frame image data object comprises pixel data associated with one or more meta-data attributes; and
   wherein the processor converting a first requested single-frame image data object and a second requested single-frame image data to the multi-frame image data standard comprises the steps of:
      (i) determining one or more shared meta-data attributes of the first and second requested image data objects by determining which of the one or more meta-data attributes of the first requested image data object and the one or more meta-data attributes of the second requested image data object are the same;
      (ii) associating the shared meta-data attributes from (i) as one entity within a multi-frame image data object; and
      (iii) associating the pixel data of the first requested image data object and the pixel data of the second requested image data object as separate entities within the multi-frame image data object.

2. The system of claim 1, wherein converting the first and second requested single-frame image data objects to the multi-frame image data standard further comprises the steps of:
   (iv) determining one or more per-frame meta-data attributes of the first and second requested image data objects by determining which of the meta-data attributes of the first requested image data object and the meta-data attributes of the second requested image data object are different; and (v) associating the per-frame meta-data attributes from (iv) as separate entities within the multi-frame image data object.

3. The system of claim 1, wherein the processor is further configured to:
   determine one or more additional sets of negotiation particulars of the negotiation; and
   determine whether to convert the one or more requested image data objects based on the first set of negotiation particulars and the one or more additional sets of negotiation particulars;
   wherein the one or more additional sets of negotiation particulars comprises information relating to one or more of available bandwidth, overall sizes of requested image data objects, estimated download time, workflow image characteristics, workflow study characteristics and workflow request characteristics.

4. The system of claim 1, wherein the processor is further configured to:
   if the negotiation particulars is retrieve type and the external imaging device supports the multi-frame image data standard, determine if the requested image data objects are stored in the memory in the multi-frame image data standard;
   if the requested image data is stored in the multi-frame image data standard, transmit the requested image data objects to the external imaging device in the multi-frame image data standard;
   if the requested image data objects are stored in the single-frame image data standard:
      convert the requested image data objects from the single-frame image data standard to the multi-frame image data standard; and
      transmit the converted requested image data objects to the external imaging device in the multi-frame image data standard.

5. The system of claim 1, wherein the processor is further configured to:
   if the negotiation particulars is store type and the external imaging device supports the single-frame image data standard, convert the requested image data objects from the single-frame image data standard to the multi-frame image data standard and store the converted requested image data in the memory.

6. The system of claim 1, wherein the processor is further configured to:
   if the negotiation particulars is store type, the external imaging device supports the single-frame image data standard and the number of requested image data objects is above an image conversion threshold, convert the requested image data objects from the single-frame image data standard to the multi-frame image data standard and store the converted requested image data objects in the memory.

7. The system of claim 1, wherein the multi-frame image data standard is the Enhanced Multi-frame Digital Imaging and Communications in Medicine standard.

8. A method for storing image data objects at a memory and for retrieving the image data objects from the memory, each image data object being in a single-frame image data standard or a multi-frame image data standard, the method comprising:
   detecting a data transmission negotiation from an external imaging device for a workflow request for one or more requested image data objects;
   when a data transmission negotiation is detected, determining a first set of negotiations particulars of the negotiation, the first set of negotiation particulars comprising an indication of the image data standard supported by the external imaging device and an indication of a type of workflow request;
   determining whether to convert the one or more requested image data objects based on the first set of negotiation particulars; and
   if the requested image data objects is to be converted, determining whether to convert the requested image data objects to the single-frame image data standard or the multi-frame image data standard;
   wherein the external imaging device supports at least one of the single-frame image data standard or the multi-frame image data standard; and
   wherein the workflow request type is a retrieve type for retrieving one or more requested image data objects from the memory or a store type for storing one or more requested image data objects to the memory;
   wherein each single-frame image data object comprises pixel data associated with one or more meta-data attributes; and
   wherein converting a first requested single-frame image data object and a second requested single-frame image data from the single-frame image data standard to the multi-frame image data standard comprises the steps of:
      (i) determining one or more shared meta-data attributes of the first and second requested image data objects by determining which of the one or more meta-data attributes of the first requested image data object and the one or more meta-data attributes of the second requested image data object are the same;
      (ii) associating the shared meta-data attributes from (i) as one entity within a multi-frame image data object; and
      (iii) associating the pixel data of the first requested image data object and the pixel data of the second requested image data object as separate entities within the multi-frame image data object.

9. The method of claim 8, wherein converting the first and second requested single-frame image data objects to the multi-frame image data standard further comprises the steps of:
   (iv) determining one or more per-frame meta-data attributes of the first and second requested image data objects by determining which of the meta-data attributes of the first requested image data object and the meta-data attributes of the second requested image data objects are different; and
   (v) associating the per-frame meta-data attributes from (iv) as separate entities within the multi-frame image data object.

10. The method of claim 8, further comprising:
   determining one or more additional sets of negotiation particulars of the negotiation; and
   determining whether to convert the one or more requested image data objects based on the first set of negotiation particulars and one or more of additional sets of negotiation particulars;
   wherein the one or more additional sets of negotiation particulars comprises information relating to one or more of available bandwidth, overall sizes of requested image data objects, estimated download time, workflow image characteristics, workflow study characteristics and workflow request characteristics.

11. The method of claim 8, further comprising:
   if the negotiation particulars is retrieve type and the external imaging device supports the multi-frame image data standard, determine if the requested image data objects are stored in the memory in the multi-frame image data standard;

if the requested image data is stored in the multi-frame image data standard, transmit the requested image data objects to the external imaging device in the multi-frame image data standard;

if the requested image data objects are stored in the single-frame image data standard:
  convert the requested image data objects from the single-frame image data standard to the multi-frame image data standard; and
  transmit the converted requested image data objects to the external imaging device in the multi-frame image data standard.

12. The method of claim 8, further comprising:
if the negotiation particulars is store type and the external imaging device supports the single-frame image data standard, converting the requested image data objects from the single-frame image data standard to the multi-frame image data standard and storing the converted requested image data in the memory.

13. The method of claim 8, further comprising:
if the negotiation particulars is store type, the external imaging device supports the single-frame image data standard and the number of requested image data objects is above an image conversion threshold, converting the requested image data objects from the single-frame image data standard to the multi-frame image data standard and storing the converted requested image data objects in the memory.

14. The method of claim 8, wherein the multi-frame image data standard is the Enhanced Multi-frame Digital Imaging and Communications in Medicine standard.

15. A system for storing image data objects and for retrieving the image data objects, the system comprising:
  a memory for storing imaging data objects, each image data object being stored in a single-frame image data standard or a multi-frame image data standard; and
  a processor coupled to the memory configured to:
    detect a data transmission negotiation from an external imaging device for a workflow request for one or more requested image data objects;
    when a data transmission negotiation is detected, determine a first set of negotiations particulars of the negotiation, the first set of negotiation particulars comprising an indication of the image data standard supported by the external imaging device and an indication of a type of workflow request;
    determine whether to convert the one or more requested image data objects based on the first set of negotiation particulars; and
    if the requested image data objects is to be converted, determining whether to convert the requested image data objects to the single-frame image data standard or the multi-frame image data standard;
wherein the external imaging device supports at least one of the single-frame image data standard or the multi-frame image data standard;
wherein the workflow request type is a retrieve type for retrieving one or more requested image data objects from the memory or a store type for storing one or more requested image data objects to the memory;
wherein each multi-frame image data object comprises a set of one or more shared meta-data attributes and first and second pixel data; and
wherein the processor converting a requested multi-frame image data object to the single-frame image data standard comprises the steps of:
  (i) associating the shared meta-data attributes and the first pixel data of the requested multi-frame image data object within a first single-frame image data object; and
  (ii) associating the share meta-data attributes and the second pixel data of the requested multi-frame image data object within a second single-frame image data object.

16. The system of claim 15, wherein each multi-frame image data object further comprises a first per-frame meta-data attribute set corresponding to the first pixel data and a second per-frame meta-data attribute set corresponding to the second pixel data; and
wherein the processor converting the requested multi-frame image data object to the single-frame image data standard further comprises the steps of:
  (iii) associating the first per-frame meta-data attribute set with the first single-frame image data object;
  (iv) associating the second per-frame meta-data attribute set with the second single-frame image data object.

17. The system of claim 15, wherein the processor is further configured to:
  determine one or more additional sets of negotiation particulars of the negotiation; and
  determine whether to convert the one or more requested image data objects based on the first set of negotiation particulars and the additional sets of negotiation particulars;
wherein the one or more additional sets of negotiation particulars comprises information relating to one or more of available bandwidth, overall sizes of requested image data objects, estimated download time, workflow image characteristics, workflow study characteristics and workflow request characteristics.

18. The system of claim 15, wherein the processor is further configured to:
  if the negotiation particulars is retrieve type and the external imaging device supports the single-frame image data standard, determine whether the requested image data is stored in the memory in the single-frame image data standard;
  if the requested image data objects are stored in the single-frame image data standard, transmit the requested image data objects to the external imaging device in the single-frame image data standard;
  if the requested image data objects are stored in the multi-frame image data standard:
    convert the requested image data objects from the multi-frame image data standard to the single-frame image data standard; and
    transmit the converted requested image data objects to the external imaging device in the single-frame image data standard.

19. The system of claim 15, wherein the processor is further configured to, if the negotiation particulars is store type and the external imaging device supports multi-frame image data standard, store the requested image data objects in the memory in the multi-frame image data standard.

20. The system of claim 15, wherein the multi-frame image data standard is the Enhanced Multi-frame Digital Imaging and Communications in Medicine standard.

21. A method for storing image data objects at a memory and for retrieving the image data objects from the memory, each image data objects being in a single-frame image data standard or a multi-frame image data standard, the method comprising:
  detecting a data transmission negotiation from an external imaging device for a workflow request for one or more requested image data objects;

when a data transmission negotiation is detected, determining a first set of negotiations particulars of the negotiation, the first set of negotiation particulars comprising an indication of the image data standard supported by the external imaging device and an indication of a type of workflow request;

determining whether to convert the one or more requested image data objects based on the first set of negotiation particulars; and if the requested image data objects is to be converted, determining whether to convert the requested image data objects to the single-frame image data standard or the multi-frame image data standard;

wherein the external imaging device supports at least one of the single-frame image data standard or the multi-frame image data standard; and wherein the workflow request type is a retrieve type for retrieving one or more requested image data objects from the memory or a store type for storing one or more requested image data objects to the memory.

wherein each multi-frame image data object comprises a set of one or more shared meta-data attributes and first and second pixel data; and wherein converting a requested multi-frame image data object to the single-frame image data standard comprises the steps of:

(i) associating the shared meta-data attributes and the first pixel data of the requested multi-frame image data object within a first single-frame image data object; and (ii) associating the share meta-data attributes and the second pixel data of the requested multi-frame image data object within a second single-frame image data object.

22. The method of claim 21, wherein each multi-frame image data object further comprises a first per-frame meta-data attribute set corresponding to the first pixel data and a second per-frame meta-data attribute set corresponding to the second pixel data; and wherein converting the requested multi-frame image data object to the single-frame image data standard further comprises the steps of:

(iii) associating the first per-frame meta-data attribute set with the first single-frame image data object;

(iv) associating the second per-frame meta-data attribute set with the second single-frame image data object.

23. The method of claim 21, further comprising:

determining one or more additional sets of negotiation particulars of the negotiation; and determining whether to convert the one or more requested image data objects based on the first set of negotiation particulars and the one or more of additional sets of negotiation particulars;

wherein the one or more additional sets of negotiation particulars comprises information relating to one or more of available bandwidth, overall sizes of requested image data objects, estimated download time, workflow image characteristics, workflow study characteristics and workflow request characteristics.

24. The method of claim 21, further comprising:

if the negotiation particulars is retrieve type and the external imaging device supports the single-frame image data standard, determining whether the requested image data is stored in the memory in the single-frame image data standard;

if the requested image data objects are stored in the single-frame image data standard, transmitting the requested image data objects to the external imaging device in the single-frame image data standard;

if the requested image data objects are stored in the multi-frame image data standard:

converting the requested image data objects from the multi-frame image data standard to the single-frame image data standard; and transmitting the converted requested image data objects to the external imaging device in the single-frame image data standard.

25. The method of claim 21, further comprising:

if the negotiation particulars is store type and the external imaging device supports multi-frame image data standard, store the requested image data objects in the memory in the multi-frame image data standard.

26. The method of claim 21, wherein the multi-frame image data standard is the Enhanced Multi-frame Digital Imaging and Communications in Medicine standard.

* * * * *